(12) United States Patent
Encarnación Martínez et al.

(10) Patent No.: US 11,911,652 B2
(45) Date of Patent: Feb. 27, 2024

(54) ERGOMETRIC TREADMILL FOR SPORT TRAINING

(71) Applicant: Bodytone International Sport, S.L., Murcia (ES)

(72) Inventors: Alberto Encarnación Martínez, Murcia (ES); Rafael Berenguer Vidal, Murcia (ES); Antonio García Gallart, Murcia (ES); Francisco Alberto Rodríguez Mayol, Murcia (ES); José Joaquín Pernías Reverte, Murcia (ES); Pedro Pérez Soriano, Murcia (ES)

(73) Assignee: Bodytone International Sport S.L., Murcia (ES)

( * ) Notice: Subject to any disclaimer, the term of this patent is extended or adjusted under 35 U.S.C. 154(b) by 1002 days.

(21) Appl. No.: 16/837,602

(22) Filed: Apr. 1, 2020

(65) Prior Publication Data

US 2020/0353309 A1    Nov. 12, 2020

(30) Foreign Application Priority Data

May 7, 2019    (EP) .................................... 19382344

(51) Int. Cl.
*A63B 22/02*    (2006.01)
*A61B 5/00*    (2006.01)
*A61B 5/22*    (2006.01)

(52) U.S. Cl.
CPC ............ *A63B 22/02* (2013.01); *A61B 5/0002* (2013.01); *A61B 5/22* (2013.01); *A61B 5/7257* (2013.01); *A61B 5/742* (2013.01)

(58) Field of Classification Search
CPC ......... A61B 5/22; A61B 5/1038; A61B 5/112; A63B 2071/0652; A63B 22/03
See application file for complete search history.

(56) References Cited

U.S. PATENT DOCUMENTS 5,368,532 A    11/1994 Farnet
6,572,512 B2    6/2003 Anderson et al.
(Continued)

FOREIGN PATENT DOCUMENTS

DE    102010003342 A1 *    9/2011    ......... A63B 22/0235
WO    2014179707 A1    11/2014
(Continued)

OTHER PUBLICATIONS

English Translation of DE-102010003342-A1, Sep. 2011, De, Harrer F, A63B22/0235 (Year: 2011).*
(Continued)

*Primary Examiner* — Sean P Dougherty
(74) *Attorney, Agent, or Firm* — CRGO Global; Steven M. Greenberg

(57) ABSTRACT

An ergometric treadmill for sport training comprising a screen, a control system and a system configured for collecting, processing, analyzing and visualizing the biomechanical response of a sportsperson while running on the ergometric treadmill; wherein the ergometric treadmill comprises (a) a plurality of MEMS sensors attached by means of supports to the ergometric treadmill connected to a data capture unit; and (b) a data processing unit configured to generate a plurality of parameters related to the physical exercise performed on the ergometric treadmill by a user and synthesize and show, in graphic form, the parameters generated for the user's biofeedback from the treadmill.

7 Claims, 9 Drawing Sheets

(56) References Cited

U.S. PATENT DOCUMENTS

| | | |
|---|---|---|
| 7,410,449 B2 | 8/2008 | Yeh |
| 7,544,153 B2 | 6/2009 | Trevino |
| 2010/0009349 A1 | 4/2010 | Watterson et al. |
| 2014/0157892 A1* | 6/2014 | Matsuzawa ........... G01L 9/0008 310/309 |

FOREIGN PATENT DOCUMENTS

| | | |
|---|---|---|
| WO | 2017011464 A1 | 1/2017 |
| WO | 2019030687 A1 | 2/2019 |

OTHER PUBLICATIONS

European Search Report dated Apr. 10, 2019 in related International Application No. 19382344.0-1115.

\* cited by examiner

ERGOMETRIC TREADMILL FOR SPORT TRAINING

CROSS REFERENCE TO RELATED APPLICATIONS

This application claims priority to EP 19382344.0, filed on May 7, 2019, the contents of which are hereby incorporated by reference in their entirety.

FIELD OF THE INVENTION

The technical field of this invention lies within the sector of computerised sports equipment and, in particular, within equipment that allows the instrumentation, recording and monitoring of the biomechanical response during sporting activity.

BACKGROUND TO THE INVENTION

This invention refers to an ergometric training treadmill in accordance with claim 1. More specifically, the object of this invention is an integrated system for collecting, processing, analyzing and visualizing the biomechanical effects produced while running on a treadmill by means of the use of sensors installed on the ergometric treadmill itself with a system for fitting MEMS—a micro-electromechanical system—accelerometers such that runners are provided with biomechanical information about their performance in order to prevent sports injuries.

Running is one of the most widely practised sporting activities worldwide and one of the most common ways of taking exercise. Running is the fourth most practised activity in Spain, both for men (14.4%) and women (11.9%) according to Ministry of Education, Culture and Sport data [MECD, 2015].

In contrast to the numerous benefits of running, it is worth noting that this activity has a high incidence of injuries, since between 40% to 50% of people that regularly go out running, injure themselves each year. On the other hand, it is important to emphasise that, during running,—with each contact of the foot with the ground or treadmill—a pair of collision forces, called force of impact, occurs.

The force of impact is defined as the force resulting from the collision between two bodies in a relatively short time period with an intensity comprising between 1.5-and-5 times body weight. This force of impact will be transmitted, spread and absorbed by the whole musculoskeletal system, from head to foot. Furthermore, the impacts have been related to the risk of suffering stress injuries during the activity since they are considered to be one of the most important types of mechanical stress from the point of view of the effect it creates in the human body.

Thus, during a typical 30-minute run, around 500 impacts may be produced or, with the accumulation of a weekly distance of 32 kilometers, runners may receive more than a million impacts. Hence, the probability of suffering stress or over-exertion injuries due to the presence of an excessively high acceleration impact, an asymmetrical distribution between the magnitude of the acceleration impacts for each leg or a reduced capacity to mitigate acceleration impacts.

Traditionally, the most widely used technique for recording impacts while running is accelerometry. By means of placing low-mass inertial sensors, the acceleration or deceleration response of a body segment can be recorded, measuring the changes in velocity a mass experiences during physical/sporting activity, recording each load as «g» or g-force (1 g=9.8 m/s$^2$).

The acceleration impacts recorded during running are made up of, basically, two components, one passive and the other active. The passive component is linked to the severity of the impacts and the appearance of sports injuries. The active component represents the magnitude of force/acceleration that the sportsperson can apply to the ground to improve his/her efficiency or performance. Furthermore, the acceleration impacts produced each time the foot comes into contact with the ground are composed internally by high or low frequency components.

As mentioned above, by using an accelerometer while running, it is possible to record acceleration impacts. Approximately, between 10%-12% of the total time that a runner's foot is in contact with the ground, a high frequency acceleration component is transmitted to the body, which presents a high load ratio. The high frequency acceleration component is considered to be a passive component since this acceleration/force, due to its magnitude (from 1 to 5 times body weight) and its short duration (25 to 50 ms from contact of the foot with the ground), the sportsperson is unable to modulate or voluntarily reduce said magnitude, the musculoligamentous structures being those responsible for reducing or absorbing said magnitude in order to prevent it from spreading to upper organs—the head, for example—and thus prevent disruption to the control organs.

In other words, the high frequency acceleration component is produced in such a reduced period of time that it cannot be controlled by means of variations to muscle activation, which is why it is not possible to control body segment rotations during the first passive phase through muscle activation.

Once the first milliseconds of force/acceleration with the ground are transmitted, the low frequency component, also known as voluntary, is produced. The low frequency component occurs, approximately, between 60% and 75% of the time that a runner's foot is in contact with the ground, with an approximate duration of 200 ms. Owing to the active force/acceleration time being relatively prolonged, they are considered as low frequency components, being influenced by the movement of the center of mass during running and this, in turn, by the voluntary action of the runner. These low frequency components are commonly known as the force a sportsperson applies on the ground to jump or run more or less quickly.

To date, all the studies that analyze the impacts of acceleration during running using accelerometry, locate the sensors directly on the sportsperson and the biofeedback system is used as an external element to the instruments used to perform the activity. There are various inventions and products that improve the features of ergometric treadmills, including sensors on different points and elements of said treadmills. In most cases, the purpose is to determine the position of the runner in order to regulate the speed of the treadmill according to the speed of the runner or even stop it in case the runner falls over.

Among the documents that describe the current state of the art, we have document US2010093492A1 that uses proximity sensors to detect whether there is any object near the treadmill that may interfere with its operation. On the other hand, documents U.S. Pat. No. 7,410,449B2, U.S. Pat. Nos. 5,368,532, 7,544,153, 6,572,512B2 and WO2017/011464A1 use optical or infra-red wavelength sensors to detect the position of the runner and allow the speed of the treadmill to be regulated or stop it should the runner stop running.

Document WO2019/030687 describes the use of infra-red sensors to detect changes in length of the lower segments and to thus determine the contact phases during the running cycle. By contrast, documents U.S. Pat. Nos. 5,368,532 and 7,101,319 describe solutions wherein optical sensors are replaced by pressure sensors to give ergometric treadmills certain functionalities. Specifically, speed control and automatic stopping of the treadmill are the main functions obtained with the data from said sensors.

Documents WO2017/011464A1 and WO2014/179707A1 describe solutions for monitoring sports performance, generally through the instrumentation of different mobile mass machines that the sportsperson activates voluntarily allowing the application of the force applied during weightlifting to be recorded or allowing the monitoring of training plans to subsequently present variables to their sporting competence/performance in peripheral applications. Similarly, document WO2017/011464A1 presents a force platform system to determine the position of the runner's foot.

In no document found in the state of the art are sensors used to determine the parameters indicated in the proposal, but sensors are used to regulate the speed of the treadmill automatically, to stop it in case of accident, to assess sports performance and similar applications. Similarly, in no document is a computerised sports system integrated into a treadmill presented that allows the biomechanical response of acceleration impacts to be presented, as well as other spatio-temporal parameters, without the need to manually place instruments on the runners wherein all the processes pertaining to the acquisition and processing of the information are processed automatically and without the need to identify the runners.

Acceleration impacts during running have been widely studied scientifically by locating acceleration sensors on the sportsperson, mainly on areas of the tibia and head. Likewise, it has been proven that providing runners with information, in real time, about their acceleration impact levels, they have been able to reduce maximum acceleration magnitudes, as well as any possible asymmetry in the distribution of acceleration between legs, making the running technique more efficient or economic. This feedback process is known as biofeedback, it being possible to provide it auditorily or visually. The implementation of biofeedback is an effective measure for reducing impacts, asymmetries and improving running economy.

Biofeedback allows runners to improve biomechanical response and prevent possible sporting injuries. However, with current technology, the implementation of this method involves (a) placing instruments with acceleration sensors on runners manually and (b) developing external applications that allow said accelerometers by cable or wirelessly, resulting in the biofeedback becoming an interesting, but difficult to use, technological resource. It is for this reason that only centers specialised in sporting biomechanics have been capable of applying said procedures, making it difficult for the general population of runners to access systems with these characteristics.

A treadmill that integrates accelerometry sensors to provide the runner with biofeedback that does not use accelerometry sensors that must be attached to the runner's extremities, which greatly complicates the practical use of the same, limiting them to experimental or scientific studies with a limited number of subjects, is not known in the state of the art. Specifically, the sensors of the state of the art are attached with tape to the extremities, transmitting the signal by cable to a data collection unit. This unit subsequently sends the data by means of some kind of wireless protocol to a computing device that allows said data to be analyzed. The analysis is normally undertaken off-line, which prevents a real-time study that provides the above-mentioned biofeedback. Furthermore, taking physical exercise by running with sensors attached to the runner is hugely inconvenient: the pressure of the sticky tape, hanging cables joining the sensors to the data-collection unit, the attachment and weight of the portable data unit during running. This makes it inconvenient for normal users to use these devices in their usual running activity.

Similarly, the process of acquiring, processing, analyzing and presenting the data in real time generates difficulties due to technological and procedural limitations inherent to computerised sporting systems. It being thus impossible to provide access to said information to any type of runner, whether professional or recreational, due to the limitations that exist with respect to the need for professionals to help with the attachment of the accelerometers and the processes for acquiring, processing, analyzing and presenting the biomechanical response to acceleration impacts during running.

SUMMARY OF THE INVENTION

An object of this invention is to provide an ergometric treadmill for sport training that allows the acquisition, processing, analysis and presentation of the biomechanical response during running in real time that overcomes the limitations described in the state of the prior art. This objective is achieved by means of the invention as defined in claim 1. Other aspects of the invention are described in other independent claims. Preferred or particular embodiments of the different aspects that make up this invention are defined in the dependent claims.

Another object of this invention is the monitoring of the biomechanical response resulting from contact between the foot and the ground relating to high frequency components and associated with sports injuries. This monitoring provides the sportsperson with the information required about his/her mechanical response, leaving out active components related to sports performance.

Another object of the invention is to use the previously monitored information to extract other variables of a spatio-temporal nature—running frequency, step lengths, asymmetry between legs or others—that provide a runner with a rapid and simple view of his/her biomechanical response, allowing him/her to adjust his/her technical execution and, thus, modulate his/her response in order to prevent injuries associated with asymmetries or excessive levels of acceleration impacts.

This invention facilitates the processing, analysis and presentation/visualization of acceleration impacts in real time by means of the use of accelerometry sensors during running on an ergometric treadmill. Furthermore, the use of a computerised system for analyzing acceleration impacts, in other words, the application of concurrent biofeedback, allows involuntary adaptations by the runners, generating benefits such as a reduction in impacts and their accelerations, as well as improving running economy, among other actions. Furthermore, by means of these accelerometry signals, it is possible to calculate other parameters that allow other running defects to be assessed. Similarly, in the future it will be possible to study accelerometry data automatically by using Big Data analysis and automatic learning (Machine Learning).

More specifically, in this invention, the IT system is integrated into a running treadmill and does not use sensors that need to be attached to runners' extremities. Furthermore, the IT system integrated into the running treadmill allows the user to be offered reliable and instant data about the mechanical stress received while running without the need for additional instrumentation on the sportsperson. All this through the acquisition, processing, analysis and presentation of the biomechanical response while running in real time. To this end, this invention includes a unit for acquiring and processing the signals from the sensors, a system for projecting/viewing, an interface for controlling the variables of the ergometric treadmill (speed and inclination) and from two to four acceleration sensors, not excluding other sensors that record the passive response to an impact with the ground during running (for example, dynamometric sensors).

The unit for acquiring and processing will have a system programed that will allow the capture and processing of the data from the signals received, generated by the impact caused by the runner on the treadmill while running. The unit will collect the information coming from the sensors (the acceleration signal) and from the ergometric treadmill, previously entered by the runner into the interface (speed of the treadmill, inclination and biophysical characteristics entered by the runner into the system). The interface will serve to manipulate the speed and inclination of the ergometric treadmill, as well as for entering the biophysical characteristics of the runners, not including said information neither being compulsory or exclusive.

The projection/viewing system will serve to represent the information collected from the sensors fitted to the ergometric treadmill and the variables calculated based on these signals, providing the user with visual feedback through a graphic interface on a screen associated with the treadmill.

The sensors (in one practical embodiment there will be two, in another practical embodiment there will be four) will be securely installed underneath the ergometric treadmill joined to the board on which the athletes run. These sensors will be directly connected by cable to the acquisition and processing unit, enabling them to be powered by the same unit, without the need for a battery that will need to be regularly charged externally by the user.

This invention describes a way of overcoming the limitations of current accelerometry measurement systems for providing users with biofeedback wherein the accelerometry sensors are in the ergometric treadmill itself and wherein the signals are processed within the same device. This implies several significant benefits: (a) it is not necessary to place sensors on the runner him/herself, significantly simplifying the measurement of the signals at all times and obtaining feedback about the run instantly; (b) experience in placing and using the sensors is not necessary since the ergometric treadmill would provide everything required for the measurement, processing and providing the runner with feedback about his/her running parameters; (c) convenience is increased for the user since the user would not need to wear any sensors or wearable capture equipment; (d) measurement precision could be uniform since these sensors can be calibrated during the manufacturing process, providing uniform measurements during all use of the device; (e) the processing equipment can be included in the ergometric treadmill itself, any other external calculation equipment being unnecessary; (f) the biofeedback system can be integrated into the ergometric treadmill itself, taking advantage of the touch screen, which is common in this type of device; (g) it will not be necessary to recharge the power of the sensors or the system since the sensors will be connected to the processing unit and this will be powered by the treadmill's own electric current; (h) it allows the acceleration impacts received by the runner while he/she is running on the treadmill to be analyzed in real time; (i) the processing unit will detect, through analysis of the signals recorded, asymmetries in the spatio-temporal variables and acceleration impacts; (j) the system will not require the prior identification of the runners for its correct operation as the system will be securely integrated into the treadmill; (k) the system will implement online processing of big data to detect patterns and correction through automatic learning (Machine Learning).

This invention, defined by its claims, offers the user reliable and instant data about the mechanical stress he/she receives while he/she is running or walking. The data are processed automatically, without the need for additional instrumentation on the sportsperson and offering the information in graphic form directly integrated into the treadmill screen. Among the basic information provided, this invention processes the maximum impacts of each leg, as well as the difference between the impacts of each leg.

Thus, by means of the visual and auditory representation through graphics and messages or audio alerts, each user will know the mechanical stress received while he/she is running or walking or if the impact is received equally between each leg. Should this not be the case and the impact received were excessive and/or the difference of the impact between the left and right leg exceeds a certain threshold, the system will inform the user so that he/she can try to reduce these parameters. Thus, this results in the impacts or stress received during an activity as widely practised and beneficial for health as running being less severe and with better bilateral load sharing, making running safer and more efficient for users.

Throughout the description and claims, the word «comprises», and its variants do not purport to exclude other technical characteristics, components or steps. For those skilled in the art, other objects, benefits and characteristics of the invention will be deduced partly from the invention and partly from using the invention. The following examples and drawings are provided by way of illustration and do not purport to restrict this invention. Furthermore, the invention covers all possible combinations of particular and preferred embodiments indicated herein.

BRIEF DESCRIPTION OF THE DRAWINGS

The following very briefly describes a series of drawings that help to understand the invention better and which expressly relate to one embodiment of said invention, which is illustrated as a non-limiting example of it.

DETAILED DESCRIPTION OF THE INVENTION

Figure 1:
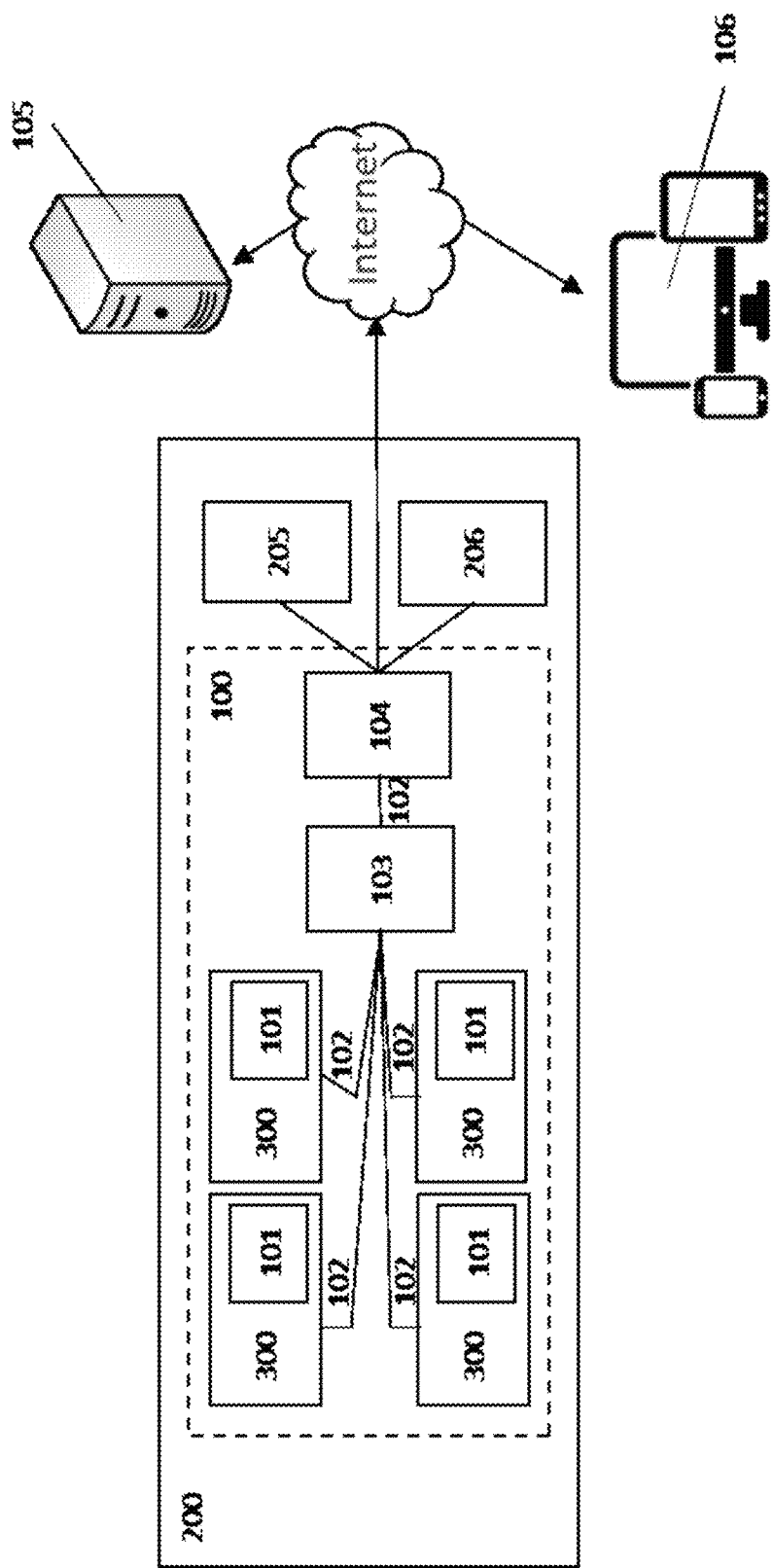
FIG. 1 shows a simplified block diagram of the integrated system for collecting, processing, analyzing and visualizing integrated into the ergometric treadmill for sport training that is object of this invention.
Figure 2:
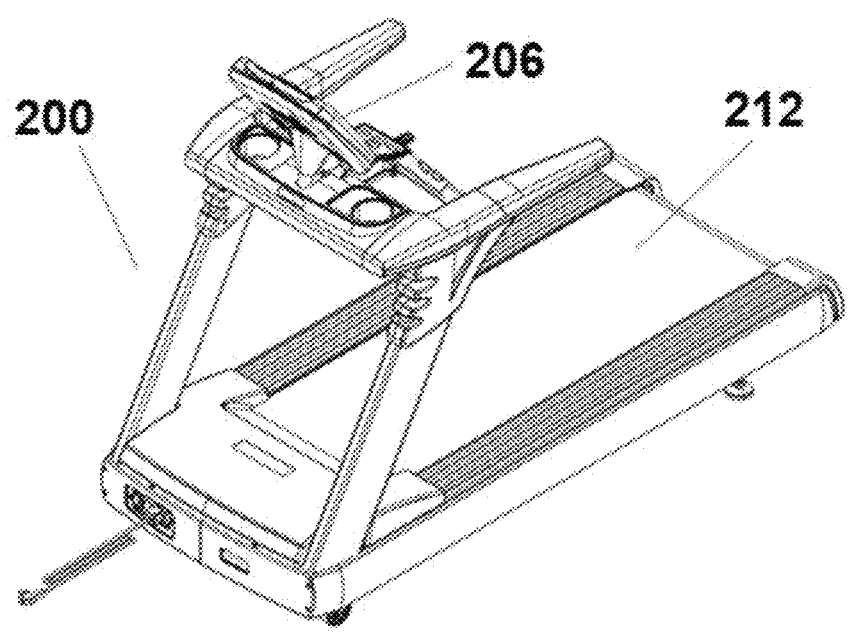
FIG. 2 shows a perspective view of the ergometric treadmill for sport training that is the object of this invention.
Figure 3:
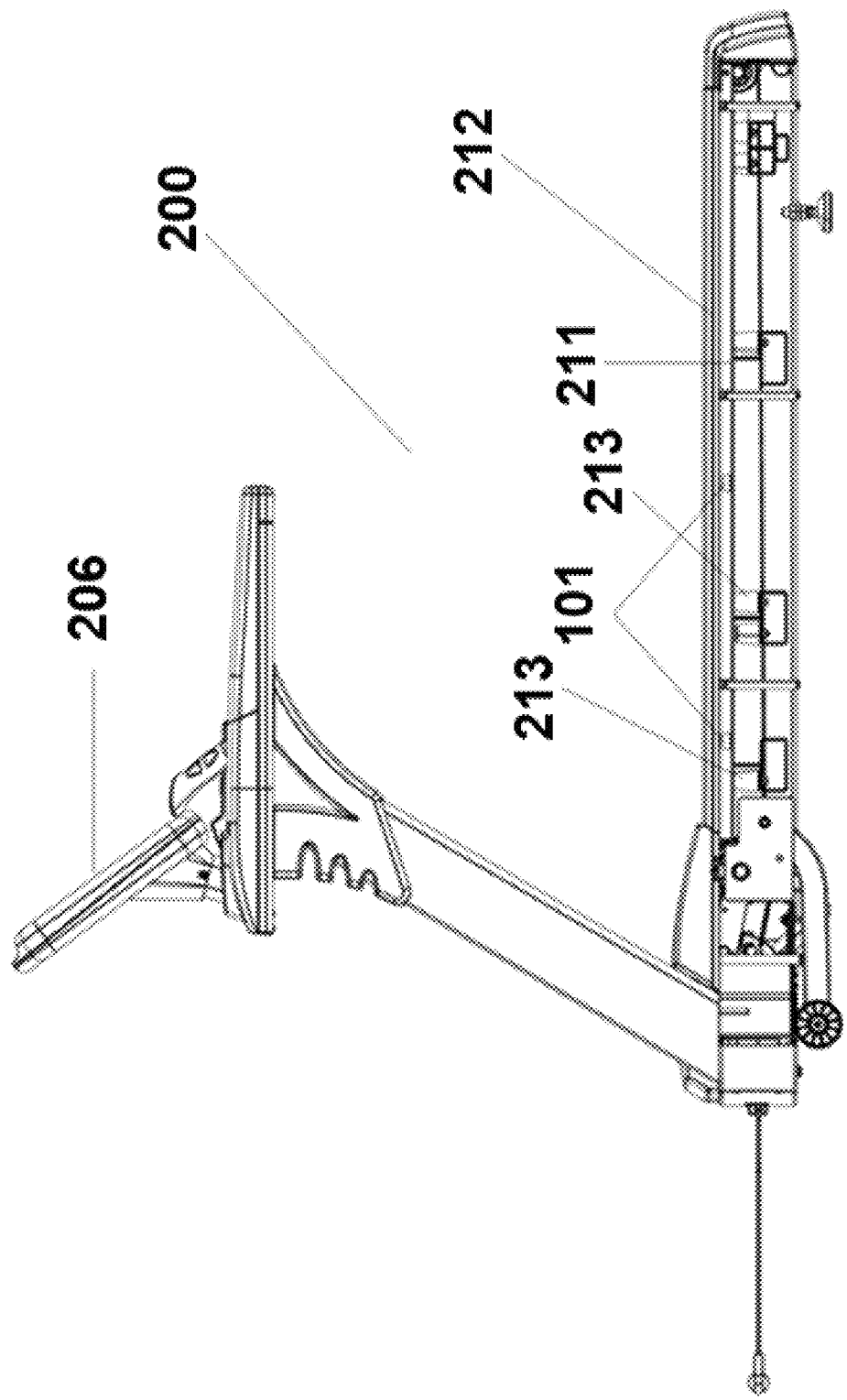
FIG. 3 shows an elevational view of the treadmill of FIG. 2 wherein one of the side covers has been removed to enable the internal elements of the treadmill to be observed better.
Figure 4:
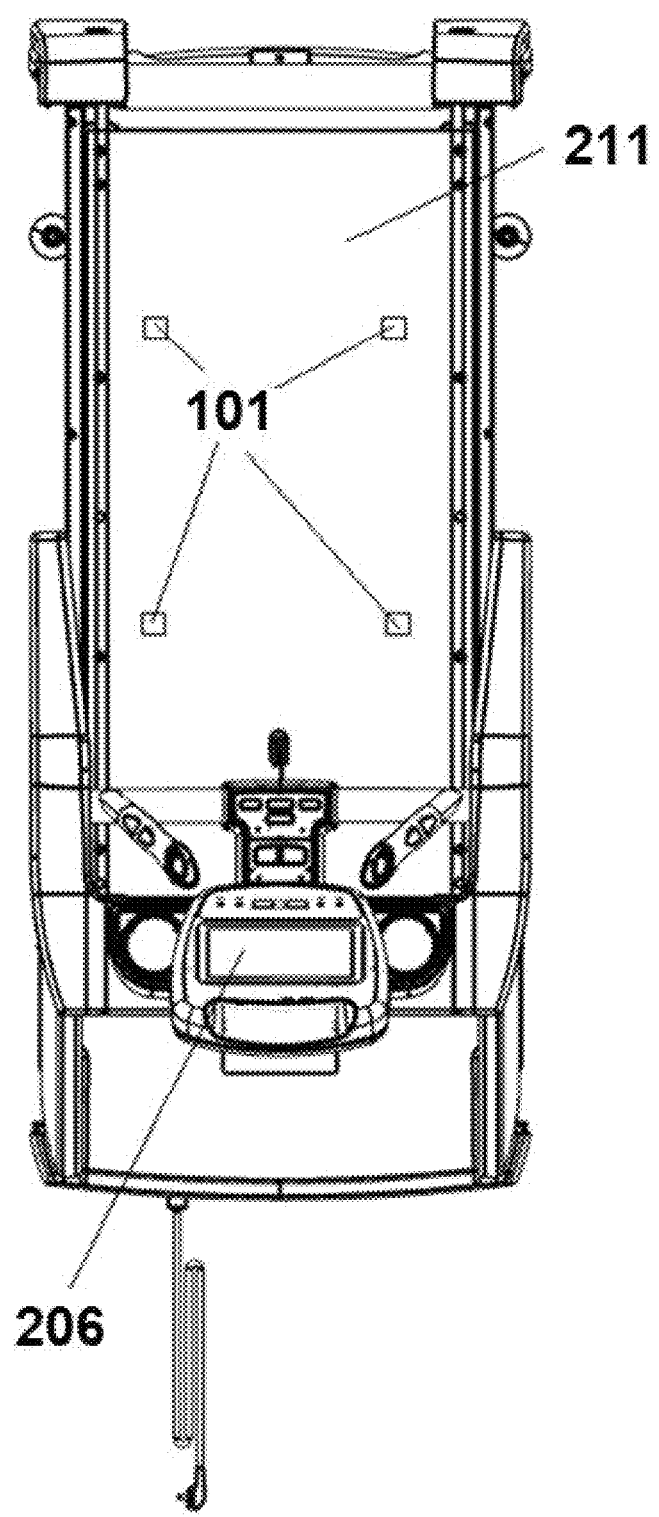
FIG. 4 shows a plan view of the treadmill of FIGS. 2 and 3 wherein the covers, protection and belt have been removed, it being possible to observe the disposition of the sensors on the belt in an embodiment with four sensors.
Figure 5:
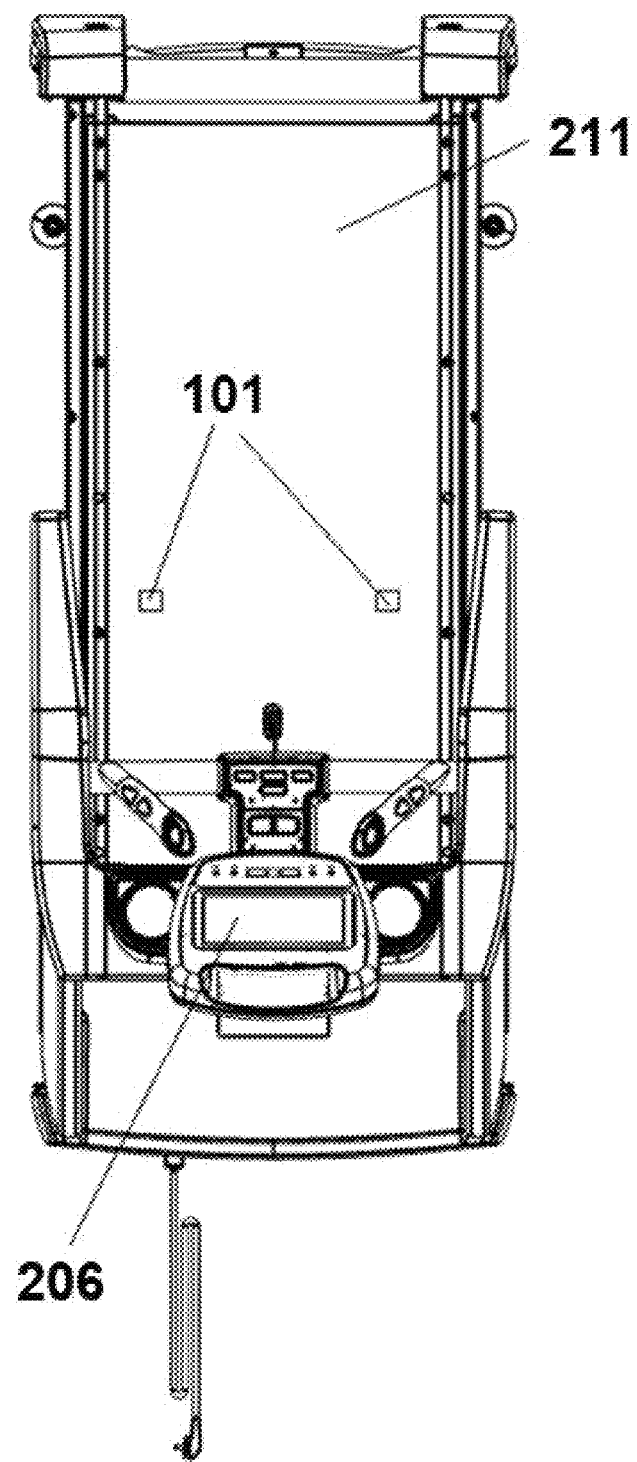
FIG. 5 shows the same image as FIG. 4 but with only two sensors.

As can be seen in the enclosed figures, the object of the invention is an ergometric treadmill (200) for sport training that integrates a system (100) configured for collecting, processing, analyzing and visualizing the biomechanical response of the sportsperson while running on the treadmill (200). The system (100) executes a method or procedure (700) for collecting, processing, analyzing and visualizing the biomechanical response of the sportsperson while running on the ergometric treadmill (200).

One of the benefits of the ergometric treadmill (200) of this invention is that the MEMS acceleration sensors (101) are attached by means of supports (300) to the ergometric treadmill itself (200), it not being necessary to place external sensor instruments on the sportsperson and allowing the evaluation and/or practise of the sport with the information about the biomechanical response of the activity undertaken provided to any type of person—and not necessarily a professional charged with its interpretation—through a screen (206) that is disposed on the ergometric treadmill itself. Furthermore, the connection by means of cables (102) of the MEMS acceleration sensors (101) to a data capture unit (103) and with a data processing unit (104) enables the power to be supplied to the whole system (100), making the use of other power sources, such as alternative batteries, unnecessary.

The ergometric treadmill (200) that is the object of the invention comprises a standard rolling belt in which a set of MEMS acceleration sensors (101) have been installed, each sensor (101) being integrated in a single support or fastening (300). The support (300) will be described in more detail below with reference to FIG. 6 and FIG. 7

The ergometric treadmill (200) includes a flat surface (211) generally a high-density wooden board over which a rolling belt (212) slides. This flat surface (211) is joined, by means of shock absorbers (213) to the structure of the ergometric treadmill (200) and receives the impacts of the runner during use of the ergometric treadmill (200). The rolling belt (212) is an endless belt that passes over and below the flat surface (211) and is connected to a motor in the front part and an axle with a tensioning system in the back part. Between the flat surface (211) and the underside of the belt (212)—which moves in the opposite direction to the upper part—a space exists where the MEMS acceleration sensors MEMS (101) are fitted. The MEMS acceleration sensors (101) are jointly connected to the flat surface (211) by means of the above-mentioned supports (300). The MEMS acceleration sensors (101) and their respective cabling (102) are located in the space comprised between the upper and lower part of the flat surface (211) and the return of the rolling belt (212), as can be best observed in FIGS. 2 to 5.

The design of the supports (300) allows the energy generated during the impact of the runner's foot on the flat surface (211) of the treadmill (200) to be captured by the MEMS acceleration sensors (101), these being recorded as a positive acceleration in the sensors (101) and inversely proportional to that suffered in the runner's extremities.

Despite the flat surface (211) being a high density board that results in the energy of the impact of the runner on the treadmill (200) being, to a large extent, transmitted to its whole surface, the vertical acceleration inflicted on the flat surface (211) will be greater on the area close to the runner's landing zone. For this reason, the inclusion of various MEMS acceleration sensors (101) in the flat surface (211) allows the acceleration suffered in each area of said flat surface (211) to be determined and, therefore, the acceleration suffered by each leg (right-left) independently.

This invention proposes two practical embodiments for the use of the MEMS acceleration sensors (101). In the first practical embodiment (FIG. 4), four MEMS acceleration sensors (101) are included, distributed two-by-two in the front and back parts of the flat surface (211). Each pair of MEMS acceleration sensors (101) are located equidistantly between the center and the side (left or right) of the flat surface (211). This practical embodiment with four sensors allows the accelerometry signals to be recorded for the landing and take-off of each leg (right or left) allowing these parameters to be analyzed in the processing of the previous signal.

On the other hand, the use of a simpler configuration (FIG. 5) is possible with the use of two MEMS acceleration sensors (101), these being fitted to the underside of the flat surface (211), also located between the edges and the center of it. This configuration only allows the accelerometry signals to be recorded for the landing of each leg independently. Although the number of signals is lower, it reduces the complexity and the cost of the system and is equally valid for the obtention of certain parameters.

Figure 6:
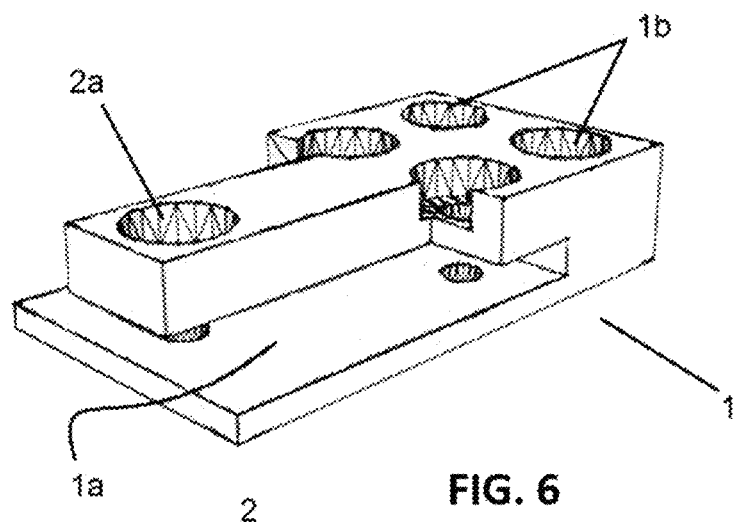
FIG. 6 shows a view of the first support part of the MEMS sensor that forms part of the system that is the object of this invention.
Figure 7:
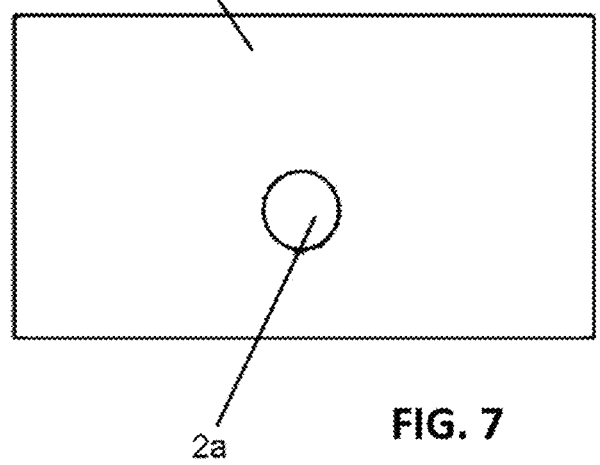
FIG. 7 shows a plan view of the second support part of the MEMS sensor that forms part of the system that is the object of this invention.

As indicated above, each MEMS acceleration sensor (101) is located in a single support (300) made up of two parts (301,302) joined together (FIG. 6 and FIG. 7). The first part (301) consists of a support per se, wherein the MEMS acceleration sensor (101) is housed—not shown in FIG. 6—in the bridge (301a) formed to enable the passage of the flat surface whose acceleration is to be measured. Thus, the part allows the insertion of the MEMS acceleration sensor (101) allowing the output of the measurement and acceleration cables (102). The first part (301) also prevents the MEMS acceleration sensor (101) from moving in the face of movements of the object—the ergometric treadmill (200)—to which it is connected. Similarly, due to its rigidity, its movement is united with the surface, the acceleration of this surface being recorded in the three Cartesian axes.

In order to prevent the flexion of the bridge (301a) in the tightening process (301b) and to prevent the MEMS acceleration sensor (101) from being able to be moved due to movement of, and knocks to, the surface and even causing the separation of the MEMS acceleration sensor (101) from the support (300), a rectangular adjustment part (302) is added to this support as shown in FIG. 7 and which is introduced into the right part of the support (300), being fastened when the support is screwed (302a) to the surface. Thus, the MEMS acceleration sensor (101) is fastened between the left part of the first part (301) and the rectangular adjustment part (302).

Figure 8:
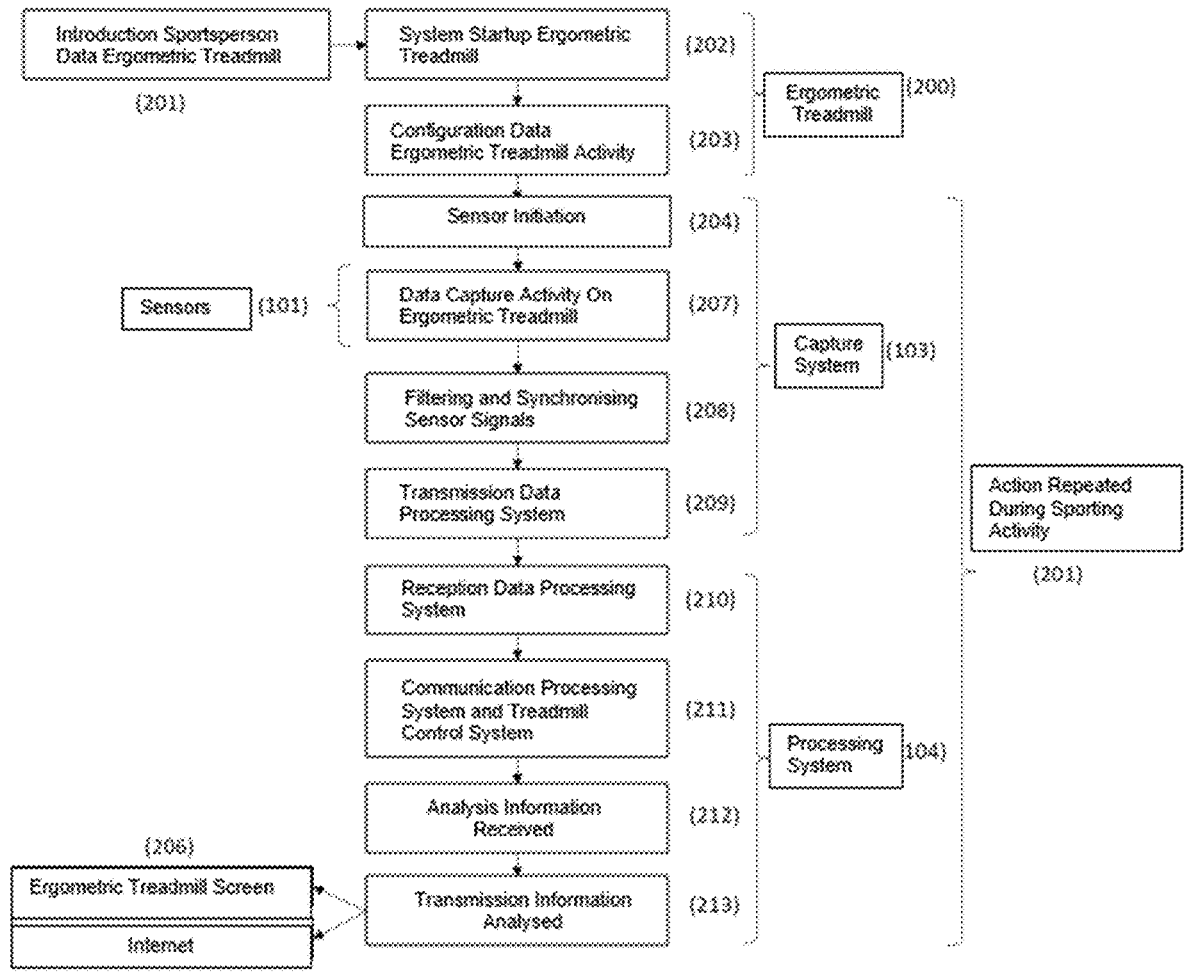
FIG. 8 shows an illustrative block diagram of the method implemented by the integrated system for collecting, processing, analyzing and visualizing installed in the ergometric treadmill for sport training that is the object of this invention.

FIG. 8 shows the general operation of the system (100) configured for collecting, processing, analyzing and visualizing the biomechanical response of the sportsperson while running on the ergometric treadmill (200). Therefore, the system (100) configured for collecting, processing, analyzing and visualizing the biomechanical response of the sportsperson while running on an ergometric treadmill (200) comprises, at least, one memory, a data processing unit (104), a screen (206), a data capture unit (103) and a plurality of MEMS sensors (101) attached by means of supports (300) to the ergometric treadmill (200), as well as a program or programs that include a plurality of instructions which, when they are executed by the processing unit (104) causes the system to execute the method described in FIG. 8.

One of the benefits of the system (100) is that it does not require the introduction of the personal data of the sportspersons (201) but does not exclude, should the sportsperson include said parameters (for example, variables such as mass, height, sex or others), the processing unit (104) from being able to transmit them subsequently. It not being necessary to introduce the parameters, any user may start up (202) the ergometric treadmill (200), configuring the desired speed and inclination (203).

The MEMS acceleration sensors (101) disposed in their respective supports (300) transmit, by means of a cabled connection (102), the unprocessed data to the data capture unit (103) that comprises, in turn, a micro-controller with various ports for sending and receiving data, a memory or memories and a program or programs that comprise a plurality of instructions which, when they are executed by the micro-controller cause the data capture unit (103) to execute the following processes: (a) it initializes and calibrates the MEMS acceleration sensors (101) disposed in their respective supports (300) when the ergometric treadmill initializes (200) and at the start of each run (204); (b) it filters (208) the signals (207) sent by each one of the MEMS acceleration sensors (101) to minimize noise and interferences; (c) it temporarily synchronizes (208) the accelerometry signals from the MEMS acceleration sensors (101) to send them (209) as a whole and grouped to the processing unit (104); and (d) it monitors (213) the data from the MEMS acceleration sensors (101) to request them to restart in the event of a problem or failure in the readings from any of them.

The flow of data from the previously filtered accelerometry signals in the data capture unit is sent jointly and synchronously (209) to a processing unit (104). The processing unit (104) receives the information (210) and is configured since it can either be an independent processor or can be emulated by the control system processes (205) of the ergometric treadmill (200).

In the event of it being independent, the control system (205) of the ergometric treadmill (200) should provide (211) the processing unit (104) with certain parameters such as, for example, the speed or the inclination of the treadmill (200), required for the correct calculation (212) of the values shown in the information feedback to the runner or biofeedback.

The processing unit (104) receives the data (210) from the data capture unit (103) and from the control system (205) of the ergometric treadmill (200), integrates the data (211), analyzes the data (212) and transmits (213) all the parameters of interest generated based on the accelerometry signals from the MEMS acceleration sensors (101) and from the control parameters of the ergometric treadmill (200). Among others, and in a non-limiting way, the processing unit (104) determines at least: the step distance in meters; the duration of the step in seconds; the frequency of the step in steps per minute or spm; the acceleration through impact expressed in g; the impact asymmetry rates (%); the distance asymmetry rates (%); and/or the indicators about the leg that presents a greater or lower level for each one of the variables.

Figure 9:
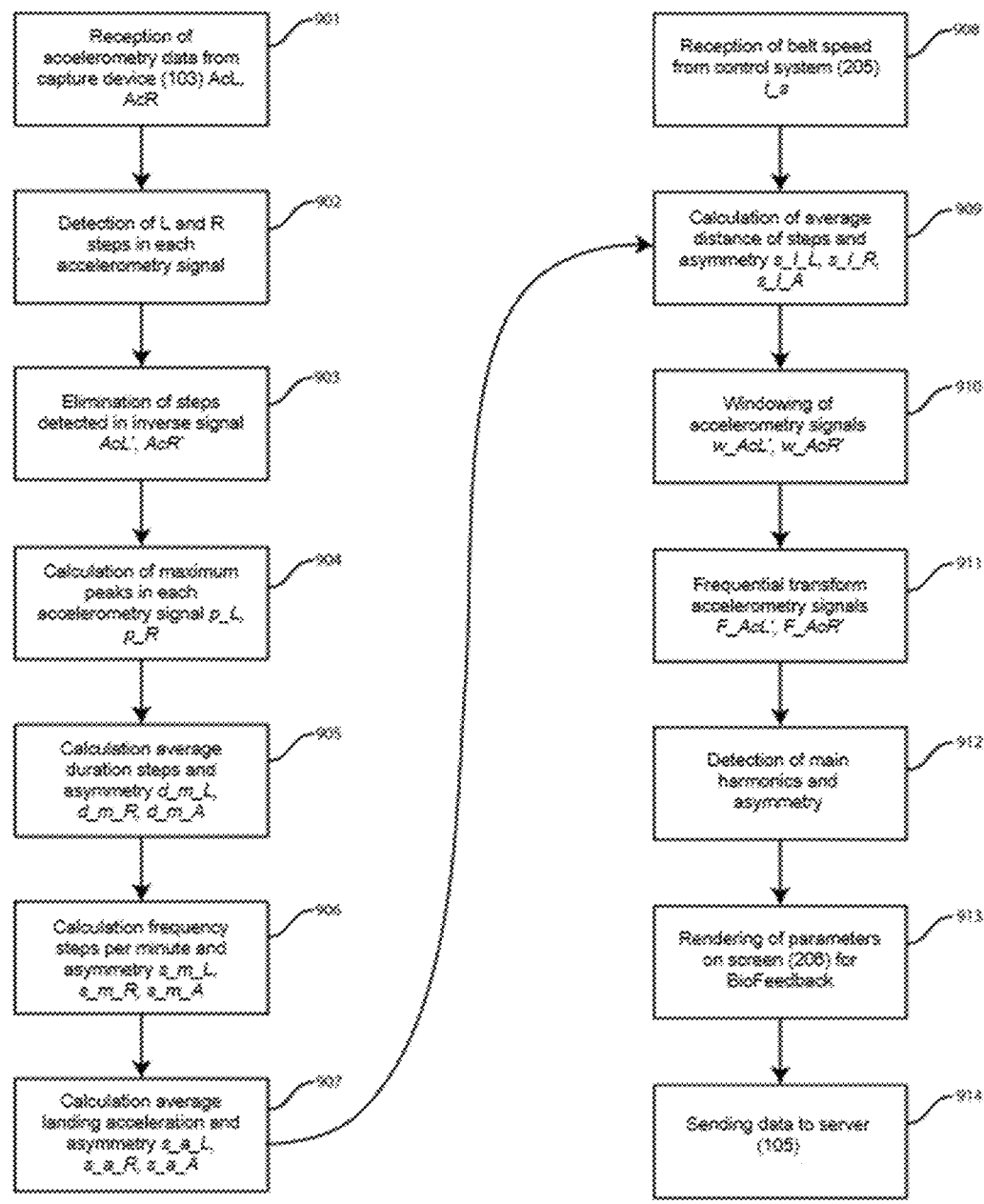
FIG. 9 shows a block diagram that illustrates the calculation algorithm executed by the processing unit that is integrated into the ergometric treadmill for sport training that is the object of this invention.

FIG. 9 shows the calculation process for the different parameters executed by the control system (205) of the ergometric treadmill (200) emulating the processing unit (104). All these are based on the accelerometry signals captured by the MEMS acceleration sensors (101), which have been filtered (208) and sent (209, 901) by the data capture unit (103) to the data processing unit (104). This diagram is specific to the system with two MEMS accelerometry sensors (101) shown in FIG. 5 but is extendible to the system equipped with four MEMS accelerometry sensors (101) shown in FIG. 4.

Based on the AcL and AcR accelerometry signals coming from the left (AcL) and right (AcR) MEMS acceleration sensors, the parameters of interest are calculated. Firstly, the peaks of the steps in each of the signals (902) are detected. Given that each accelerometry signal captures left and right steps, initially, the steps corresponding to each sensor (902) are determined and the steps corresponding to the opposite signal (903) are eliminated. Thus, the AcL' signal will only take into account the steps of the left foot and the AcR' signal will only take into account the steps of the right foot.

Figure 10:
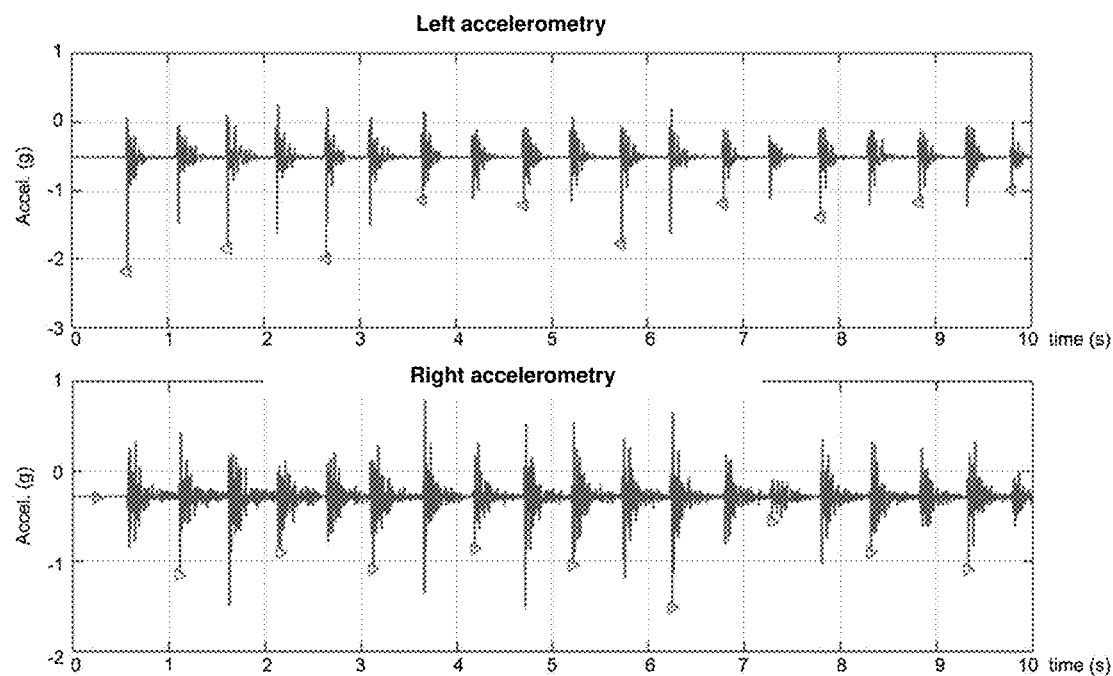
FIG. 10 and FIG. 11 show, respectively, the accelerometry signals coming from each sensor (for the two-sensor option) indicating the dominant step and the transformation to the frequency domain of said accelerometry signals for the obtention of the main harmonics and their asymmetries between left and right steps.

Below, the values of the maximum left (p_L) and right (p_R) accelerometry peaks of each step are calculated. FIG. 10 shows the two accelerometry signals (p_L and p_R), showing in each one, the steps corresponding to said sensor and which will be used in the rest of the calculation stages (905-907) and (909-912).

Based on the AcL', AcR', p_L and p_R signals, the average duration of the steps for the left (d_m_L) and right (d_m_R) legs are obtained (905) as well as the asymmetry between both legs (d_m_A). In a similar way, the frequency of steps per minute for the left (s_m_L) and right (s_m_R) legs and the asymmetry (s_m_A) are calculated (906). Subsequently, the average value of the average acceleration measured in (g) is calculated (907) of each s_a_L and s_a_R step, and their asymmetry s_a_A, To calculate (909) the average distance of s_l_L and s_l_R steps, and their asymmetry s_l_A, the speed of the belt t s is required, which is provided (908) by the control system (205) of the ergometric treadmill (200).

Figure 11:
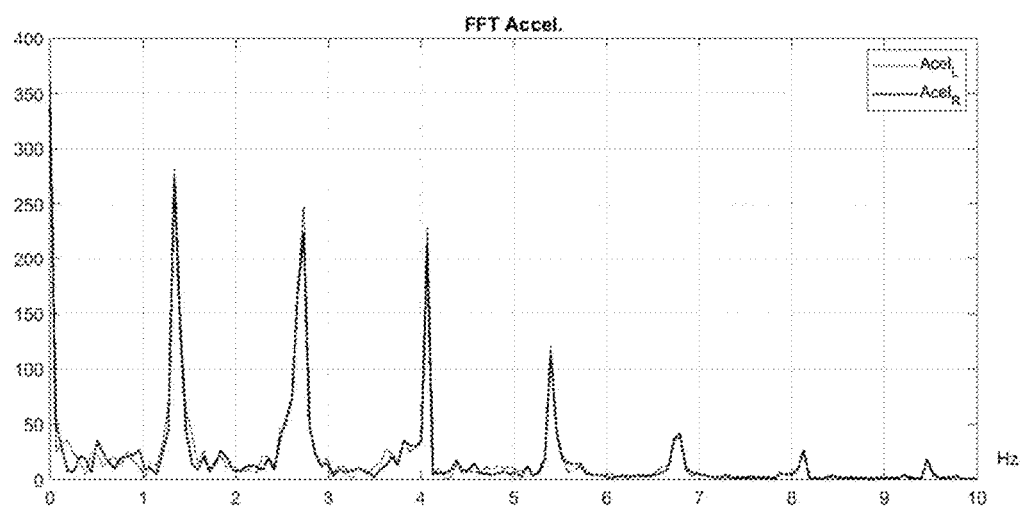

The rest of the parameters of interest are calculated in the frequency domain. Firstly, each one of the steps in each signal is processed (in windows) to guarantee that all the steps are of equal length in number of samples (910) and result in an identical spectral resolution. The signals processed in windows w_AcL' and w_AcR' are moved (911) to the frequency domain by means of the Fourier transform, obtaining F_AcL' and F_AcR'. FIG. 11 shows these two signals in the frequency domain. Based on these F_AcL' and F_AcR' signals, the most significant harmonics of the run and the asymmetry between both legs are determined (912).

Finally, the runner is shown (913), on the screen (206) of the ergometric treadmill (200), the information in real time about asymmetry and other running parameters for the purpose of generating positive biofeedback. In the same way, the data are sent through a communications network to a server (105) to be studied later using big data analysis or to be consulted by means of an external device to the ergometric treadmill (200) such as a portable device or a computer (106).

In summary, the different parameters described are calculated for the right and left legs, the average value and the value for asymmetry between both legs is determined. The parameters are synthesized and shown in graphic form using the screen of the ergometric treadmill (206), providing the runner with the biofeedback described above. Equally, according to the information provided by the user of the ergometric treadmill (age, mass, height or any other) and the running/walking speed selected, healthy impact/acceleration ranges will be calculated based on the scientific evidence available. Thus, should the user exceed said levels, the system itself would show his/her acceleration graph along with an indicator informing him/her that he/she should try to reduce impact/acceleration levels (biofeedback).

Both the accelerometry signals and the parameters calculated in each training session are sent by Internet to a server (105) along with the user's data. This allows the user to be able to download his/her data subsequently to any treadmill and thus analyze the evolution of his/her running technique over time. Equally, these data may be downloaded and visualized on a computer or portable device (106), making it possible for the user to always have access to a study of his/her parameters, thus increasing improvement in his/her running. Similarly, owing to there being a repository of data from multiple users available on the server, it is possible to perform a Big Data study, allowing the obtention of new parameters or estimations in the evolution of the runner learning from it (through the use of Machine Learning techniques). This information can be shown on the treadmill screen itself or on the user's electronic device.

Functionality as a High Dynamic Range Sensor (HDR)

One of the problems faced in the measurement of accelerometry signals for this application is the maximum range of the signal bandwidth according to which the user is walking (narrower accelerometry signal bandwidth) or running (broader accelerometry signal bandwidth). This forces an adjustment of the sensor's dynamic margin in the maximum case (user running), causing a low resolution of the sensors when the user is walking on the belt.

A second functionality consists of the duplication of sensors for the purpose of increasing the dynamic margin in the accelerometry signals measured on the belt. In this case, two sets of sensors reading simultaneously are disposed of One set is adjusted to work with high value peak accelerations and the other for lower acceleration levels. All the sensors will be calibrated precisely.

Measurements are always made from the sensors with the lower maximum value (which are more precise) and, should the sportsperson's activity cause a saturation in the measurement (by exceeding the sensor's maximum threshold) during a period of time, readings from the higher threshold sensors will be proceeded with, allowing a high dynamic range (HDR) in the accelerometry signals measured.

What is claimed is:

1. An ergometric treadmill for sport training comprising a screen, a control system and a system configured for collecting, processing, analyzing and visualizing a biomechanical response of a user while running on the ergometric treadmill, wherein the system comprises:
   (a) a plurality of microelectromechanical system (MEMS) acceleration sensors attached by supports to the ergometric treadmill connected to a data capture unit comprising a micro-controller with ports for sending and receiving data, at least one memory, and at least one program comprising a plurality of instructions which, when executed by the micro-controller, cause the data capture unit to:
      (1) initialize and calibrate the plurality of MEMS acceleration sensors disposed in their respective supports when the ergometric treadmill initializes and at the start of each run;
      (2) filter signals sent by each of the plurality of MEMS acceleration sensors to minimize noise and interference;
      (3) temporarily synchronize accelerometry signals from the plurality of MEMS acceleration sensors to send the signals from the plurality of MEMS acceleration sensors as a whole and grouped to the data processing unit; and
      (4) monitor the data from the plurality of MEMS acceleration sensors to request the MEMS accelerations sensors to restart in event of a problem or a failure in readings therefrom;
   (b) a data processing unit comprising a processor and at least one memory that stores at least one program that includes instructions that, when executed by the processor, cause the data processing unit to:
      (1) receive data from the data capture unit and the control system of the ergometric treadmill;
      (2) generate a plurality of parameters related to physical exercise performed on the ergometric treadmill by the user, wherein the plurality of parameters is calculated for left and right legs of the user, man average value of both the left and the right legs of the user, and an asymmetry level between both the left and the right legs of the user; and
      (3) synthesize and show the plurality of parameters generated in (b)(2) in graphic form in form of a loop by the screen of the ergometric treadmill.

2. The ergometric treadmill of claim 1, further comprising at least one program with instructions which, when executed by the processor cause the data processing unit to send the plurality of parameters generated in (b)(2) to an external server or an external device.

3. The ergometric treadmill of claim 1, wherein the data processing unit is emulated in the control system of the ergometric treadmill.

4. The ergometric treadmill of claim 1, wherein the plurality of MEMS acceleration sensors are disposed in their respective supports and transmit unprocessed data through a cabled connection to the data capture unit.

5. The ergometric treadmill of claim 1, wherein the support of the plurality of MEMS acceleration sensors comprises two parts connected together, wherein a first part is configured as a physical support for each of the plurality of MEMS acceleration sensors and a second part is a rectangular part screwed to the first part and each of the plurality of MEMS acceleration sensors.

6. The ergometric treadmill of claim 1, wherein the plurality of MEMS acceleration sensors comprises two MEMS acceleration sensors located in a front part of a flat surface disposed between an outward and return path of a rolling belt of the ergometric treadmill and located between edges and a center of the flat surface.

7. The ergometric treadmill according to claim 1, wherein the plurality of MEMS acceleration sensors comprises four MEMS acceleration sensors distributed two-by-two in a front part and a back part of a flat surface disposed between an outward and return path of a rolling belt of the ergometric treadmill, and wherein each pair of the four MEMS acceleration sensors is located equidistantly between a center and a left or right side of the flat surface.

* * * * *